United States Patent [19]

Hesse

[11] Patent Number: Plant 6,084

[45] Date of Patent: Jan. 19, 1988

[54] CHRYSANTHEMUM PLANT NAMED ULTRALIGHT

[75] Inventor: Peter S. Hesse, Bradenton, Fla.

[73] Assignee: Ball PanAm Plant Company, Parrish, Fla.

[21] Appl. No.: 813,772

[22] Filed: Dec. 19, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Ultralight having daisy capitulum type and flat capitulum form, dark purple ray floret color, nine week flowering response, upright growth habit, and excellent color retention at high temperatures.

1 Drawing Figure

The present invention comprises a new and distinct cultivar of *Dentrenthema morifolium*, Ramat., previously *Chrysanthemum morifolium*, Ramat., hereinafter referred to by the cultivar name Ultralight.

Ultralight is a product of a planned breeding program which had the objective of creating new Chrysanthemum cultivars with daisy capitulum type, lavender ray floret color, rapid flowering response from the start of short days, and having the ability to produce commercially acceptable quality in year around pot mum programs. Such traits in combination were not present or needed improvement in previously available commercial cultivars.

Ultralight was originated from a hybridization made in a controlled breeding program in West Chicago, Ill. in 1980. The female parent was Circus, disclosed in U.S. Plant Pat. No. 4,188. The male parent of Ultralight was Twilight, disclosed in U.S. Plant Pat. No. 5,043.

Ultralight was discovered and selected as one flowering plant within the progeny of the stated parentage by or under the supervision of Peter S. Hesse in November of 1981 in a controlled environment in Bradenton, Fla.

The first act of asexual reproduction of Ultralight was accomplished when vegetative cuttings were taken from the initial selection in February of 1982 in a controlled environment in Bradenton, Fla. by a technician working under formulations established and supervised by Peter S. Hesse. Horticultural examination of selected units initiated December of 1982 has demonstrated that the combination of characteristics as herein disclosed for Ultralight are firmly fixed and are retained through successive generations of asexual reproduction.

Ultralight has not been observed under all possible environmental conditions. The phenotype may vary significantly with variations in environment such as temperature, light intensity and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Ultralight which in combination distinguish this Chrysanthemum as a new and distinct cultivar:

1. Daisy capitulum type.
2. Flat capitulum form.
3. Very unique, dark lavender ray floret color.

4. Diameter of 2–3" across face of capitulum.
5. Upright growth habit.
6. Nine (9) week flowering response.
7. Excellent color retention at high temperature.

Of the many commercial cultivars known to the present inventor, the most similar in comparison to Ultralight is the female parent, Circus. In comparison to Circus, Ultralight is darker purple in color, has a more upright growth habit, better flower substance, is less sensitive to high or low temperatures, and has better color retention at high temperatures. The capitulum form and type and flowering response of Ultralight are similar to those same characteristics of Circus.

The accompanying photographic drawing shows typical inflorescence and foliage characteristics of Ultralight. The photograph is in black and white except for three flowers which have been colored to accurately depict the fresh flower color of Ultralight.

In the following description, color references are made to The Royal Horticultural Society Colour Chart. The color values were determined at approximately 11:00 a.m. on Nov. 20, 1985 under fluorescent light at Bradenton, Fla.

Classification:

*Botanical.*—*Denthenthema morifolium*, Ramat., cv Ultralight.

*Commercial.*—Daisy pot mum.

INFLORESCENCE

A. Capitulum:
- *Form.*—Flat.
- *Type.*—Single or daisy.
- *Diameter across face.*—2"–3".

B. Corolla of ray florets:
- *Color (general tonality from a distance of three meters).*—Dark purple.
- *Color (upper surface).*—72A-B.
- *Color (under surface).*—70D.

C. Corolla of disc florets:
- *Color (mature).*—Yellow.
- *Color (immature).*—Yellow-green.

D. Reproductive organs:
- *Androecium.*—Present in disc florets only; insignificant.
- *Gynoecium.*—Present in ray florets only; insignificant.

PLANT

A. General appearance:

*Height.*—Approximately 250–300 mm.

B. Foliage:

*Color* (*upper surface*).—147A.

*Color* (*under surface*).—147B.

*Shape.*—Deeply lobed and slightly serrated.

I claim:

1. A new and distinct cultivar of Chrysanthemum plant named Ultralight, as described and illustrated, and particularly characterized by its daisy capitulum type and flat capitulum form, dark purple ray floret color, nine week flowering response, upright growth habit, and its excellent color retention at high temperatures.

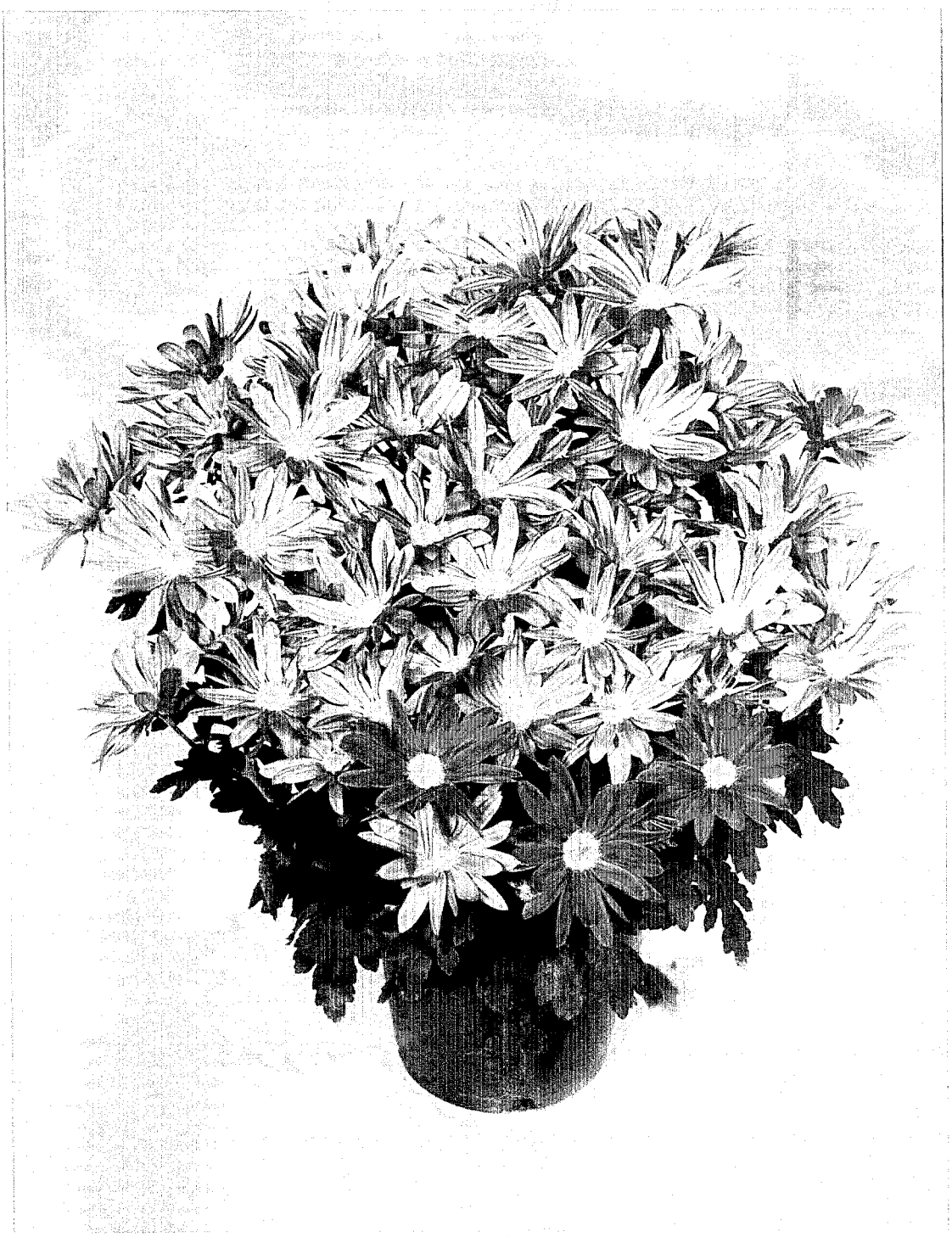

* * * * *